US007369945B2

(12) United States Patent
Miller et al.

(10) Patent No.: US 7,369,945 B2
(45) Date of Patent: May 6, 2008

(54) APPARATUS AND METHOD FOR STORING AND TRANSPORTING DATA RELATED TO VAPOR EMISSIONS AND MEASUREMENTS THEREOF

(75) Inventors: Terry Miller, Durango, CO (US); Howard Carnes, Suwanee, GA (US)

(73) Assignee: TMx2, Inc., Baytown, TX (US)

( * ) Notice: Subject to any disclaimer, the term of this patent is extended or adjusted under 35 U.S.C. 154(b) by 0 days.

(21) Appl. No.: 11/245,273

(22) Filed: Oct. 5, 2005

(65) Prior Publication Data
US 2006/0206272 A1 Sep. 14, 2006

Related U.S. Application Data

(60) Provisional application No. 60/616,308, filed on Oct. 5, 2004.

(51) Int. Cl.
G06F 17/40 (2006.01)
G06F 19/00 (2006.01)

(52) U.S. Cl. .................. 702/24; 73/23.2; 73/23.35; 73/23.38; 340/500; 340/603; 340/870.01; 340/870.07; 702/127

(58) Field of Classification Search .............. 73/23.2, 73/23.35, 23.38, 23.41, 23.42, 863; 340/500, 340/603, 605, 632, 870.01, 870.07; 702/22, 702/24, 50, 51, 127
See application file for complete search history.

(56) References Cited

U.S. PATENT DOCUMENTS

| 2,901,624 | A | * | 8/1959 | Nier | 250/300 |
|---|---|---|---|---|---|
| 3,090,038 | A | * | 5/1963 | Klein et al. | 340/515 |
| 3,266,293 | A | * | 8/1966 | Hubner | 73/23.2 |
| 3,399,974 | A | * | 9/1968 | Spencer et al. | 422/54 |
| 3,415,108 | A | * | 12/1968 | Hubner | 73/31.05 |
| 3,603,155 | A | * | 9/1971 | Morris et al. | 73/863.01 |
| 3,721,825 | A | * | 3/1973 | Rasmussen, Jr. | 250/308 |
| 3,852,730 | A | * | 12/1974 | Commins | 340/870.05 |
| 4,088,985 | A | * | 5/1978 | Saito et al. | 340/605 |
| 4,258,421 | A | * | 3/1981 | Juhasz et al. | 701/35 |
| 4,725,551 | A | * | 2/1988 | Thompson | 436/3 |
| 5,099,437 | A | * | 3/1992 | Weber | 702/187 |
| 5,210,702 | A | * | 5/1993 | Bishop et al. | 702/24 |
| 5,225,996 | A | * | 7/1993 | Weber | 702/187 |
| 5,356,594 | A | * | 10/1994 | Neel et al. | 422/54 |
| 5,535,136 | A | * | 7/1996 | Standifer | 702/51 |
| 5,568,121 | A | * | 10/1996 | Lamensdorf | 340/539.17 |
| 5,578,834 | A | * | 11/1996 | Trobridge | 250/551 |
| 5,831,183 | A | * | 11/1998 | Baxter et al. | 73/863.51 |

(Continued)

FOREIGN PATENT DOCUMENTS

JP    10-143782 A   *   5/1998

(Continued)

Primary Examiner—Edward R Cosimano
(74) Attorney, Agent, or Firm—Fulbright & Jaworski LLP

(57) ABSTRACT

The present invention provides apparatus and a methods for collecting, transmitting and storing fugitive gas emission data. An embodiment of the invention collects fugitive gas with a sampling probe and into a emission monitoring device. The device then sends and stores fugitive gas data into a storage medium, such as a wireless data-logging adapter. The wireless-data logging adapter stores the data and wirelessly sends it to a personal digital assistant or other form of redundant memory such as a data logger. In one embodiment, the PDA can initiate commands to retrieve data from the storage medium or operate the emission gas monitoring device.

15 Claims, 3 Drawing Sheets

U.S. PATENT DOCUMENTS

| | | | |
|---|---|---|---|
| 5,892,690 A * | 4/1999 | Boatman et al. | 700/276 |
| 6,182,497 B1 * | 2/2001 | Krajci | 73/23.2 |
| 6,198,400 B1 * | 3/2001 | Church et al. | 340/632 |
| 6,266,995 B1 * | 7/2001 | Scott | 73/23.2 |
| 6,285,955 B1 * | 9/2001 | Goldwasser | 702/6 |
| 6,289,288 B1 * | 9/2001 | Kraft | 702/23 |
| 7,006,923 B1 * | 2/2006 | Rubin | 702/19 |
| 7,080,544 B2 * | 7/2006 | Stepanik et al. | 73/31.02 |
| 7,183,115 B1 * | 2/2007 | Lauglin | 436/38 |
| 2004/0075566 A1 * | 4/2004 | Stepanik et al. | 340/632 |
| 2006/0093523 A1 * | 5/2006 | Norman | 422/83 |
| 2006/0273895 A1 * | 12/2006 | Kollin | 340/539.17 |

FOREIGN PATENT DOCUMENTS

| | | | |
|---|---|---|---|
| JP | 2000-193651 A | * | 7/2000 |
| WO | WO 02/073161 A1 | * | 9/2002 |

* cited by examiner

APPARATUS AND METHOD FOR STORING AND TRANSPORTING DATA RELATED TO VAPOR EMISSIONS AND MEASUREMENTS THEREOF

CROSS-REFERENCE TO RELATED APPLICATIONS

This application claims the benefit of U.S. Provisional Patent Application, Ser. No. 60/616,308, filed Oct. 5, 2004, now expired, the contents of which is incorporated herein by reference.

TECHNICAL FIELD

The present invention relates generally to the petrochemical and refinery field and more particularly to an apparatus and method for detecting vapor emissions and storing and transporting data related thereto.

BACKGROUND OF THE INVENTION

Petrochemical and refinery facilities move volatile fluids between processes through a complex array of pipes. Pipes are joined in tandem have sealed joints to prevent fugitive emissions. Pipes not joined in tandem have sealed end caps to avoid fugitive emissions. Conditions may be such that leaks develop at the seal points. These leaks, or fugitive emissions, are toxic and explosive and represent a threat to human life and property.

In order to avoid the dire results of pipe seal failures, state and federal law mandates frequent inspections and monitoring of pipe seals. In addition, petrochemical and refinery companies must maintain measurement logs along with fugitive vapor measurement data.

Piping in petrochemical and refinery companies facilities may have hundreds, or even thousands of pipe seals. Such seals are often difficult to access and require the use of ladders to realize a measurement. Current art utilizes a emission sampling probe which detects fugitive ionization emissions. The probe is connected to an gas transport conduit which function to transport vapor samples from the probe's aperture to an emissions measuring device, carried in the operator's backpack. An electrical cable extends from the emissions measuring device to a hand held data-logging device. The electrical cable extending from the backpack to the hand held device experiences constant flexing and stress, particularly at the electrical connector, such that normal use requires frequent cable replacements. In addition, when a cable breakdown data is lost or irreparably compromised. Data loss and cable breakdowns jeopardize pecuniary, property and personal safety interests.

It is desirable to find alternative means of data cabling and a means of increasing data reliability and accuracy by introducing data storage redundancy.

BRIEF SUMMARY OF THE INVENTION

The present invention is directed to a system and method which detects vapor emissions then stores and electronically transports data related thereto. Whereas the current art experiences failures induced by the dynamics of the measurement process and is susceptible to loss of data integrity the present invention improves both reliability and data protection.

The state of the current art utilizes a wire data cable that connects the emissions measuring device to a hand held data logging device. A sampling probe—used to detect flame ionization and fugitive emissions—is then connected to the emissions measuring device. The emissions measuring device is placed in a backpack carried by the test operator. The wire data cable exits from the emissions measuring device at backpack location to the data logging device held by the test operator. Gas transport conduit connects to the probe and exits from the backpack to the sampling probe held by the test operator.

In the course of performing tests, the wire data cable in the current art is under significant stress at the its termination points. Frequently the cable becomes damaged and may corrupt data. Eventually the cable completely fails and requires repair or replacement. This precipitates economic loss of test time and cost of material repair or replacement.

In this embodiment of the present invention eliminates the wire data cable that extends from emissions measuring device at the backpack to the tester's hand held apparatus. In place of a cable, a wireless connection is used to link the emissions measuring device to a compatible wireless data-logger device. Such data-logger device may comprise a Personnel Data Assistant (PDA) or other device with a storage medium, microprocessor and transceiver for wireless communication. The storage medium comprises any medium of sufficient capacity capable of storing binary numbers. The wireless link or connection eliminates the economic loss of the current art approach. Additionally, the emissions measuring device is coupled with an additional storage medium which serves as a redundant storage location for sample data. Such sample data is wirelessly transported to the hand held data-logger device.

In this embodiment of the invention, sample data is moved from the probe onto the storage medium then onto the hand held data-logger device. Data samples are stored storage medium and at the data-logger device. At the end of an eight-hour work shift all data are transferred from the data-logger device to a back office database for long term archiving. Sample data residing in the storage medium and the data-logger device is erased and is made ready for the next work shift.

In one embodiment of the invention, the wireless data-logging adapter ("WDA") of the emissions measuring device is designated as a server and the data-logger device as the client. Here, all manual transactions are initiated at the data-logger device under control of the test operator. There may be a plurality client data-logger devices with the functional ability to connect with one or more data-logging adapters on emissions monitoring devices acting as servers.

In one embodiment, there are three basic states. A system task state provides authentication log on and log off capability, system set-up, heart beat to verify operation, and to reset the wireless data-logger as a maintenance operation.

The reading mode state controls the probe to initiate a test sequence with a get probe Data. The test operator then moves the probe around the circumference of the pipe seal under test. Sets of discrete samples are taken as the probe is moved along the pipe seal.

Following the reading mode state is the store data state. Sample data is now stored in the emission measuring device's storage medium followed in time to the data-logger device via the wireless connection. At completion of the test shift data is downloaded to a back office database. Both memories in the storage medium and the data-logger device may be cleared of all sample data to be ready for the next test shift or as desired.

In one embodiment, the WDA executes the operational states on an electronic circuit card. Samples taken by the probe are sent to a storage medium on the WDA via a serial data link. Initiation commands to get probe data and start and stop probe sample data acquisition are sent over this same serial data link. A serial data link transceiver located in the storage medium connects to a microprocessor matrix crossbar switch. The microprocessor matrix crossbar switch may be substituted for any microprocessor capable of routing serialized probe data samples from the probe to the storage medium cache memory. Data from the cache memory is then routed on demand to the wireless server transceiver. The wireless server transceiver sends the sample data to the data-logger device via the wireless connection.

In one embodiment, the invention commands initiated by the test operator through the data-logger device are transmitted over the wireless connection to the WDA's wireless server transceiver. There, the data-logger device commands are sent to the microprocessor crossbar switch, where they are routed to the microprocessor core for interpretation and execution of the sent command.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which.

DETAILED DESCRIPTION OF THE INVENTION

Figure 1:
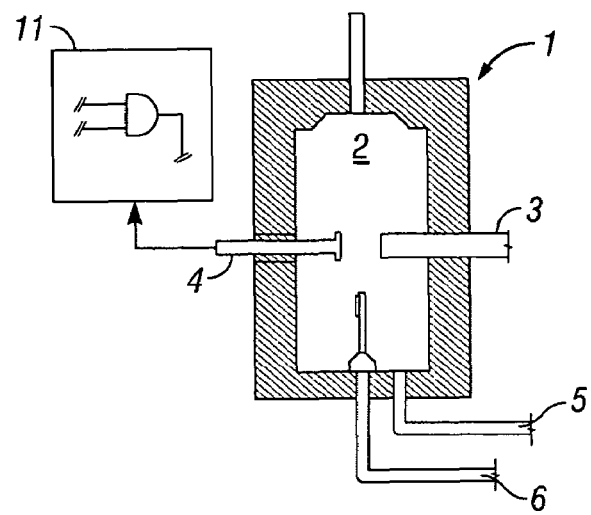
FIG. 1 shows an example of the apparatus used for detecting vapor emissions.

FIG. 1 shows the mechanical view of basic components of a typical flame ionization detector 1 used to detect vapor, gas and other fugitive emissions from pipes and pipe connections. The cavity 2 is where the fugitive gas sample 5 is drawn internally along with Hydrogen gas 6. On command from, for example, a wireless data-logger adapter, an ignition filament 3 ignites the gas mixture. A collector electrode 4 measures an ionization level that is translated into level of fugitive vapor or gas. Fugitive vapor data is digitized in the flame ionization detector electronic circuit board 11. The digitized fugitive vapor sample data is serialized and provides a serial data transceiver interface to, for example, a wireless data-logger adapter.

Figure 2:
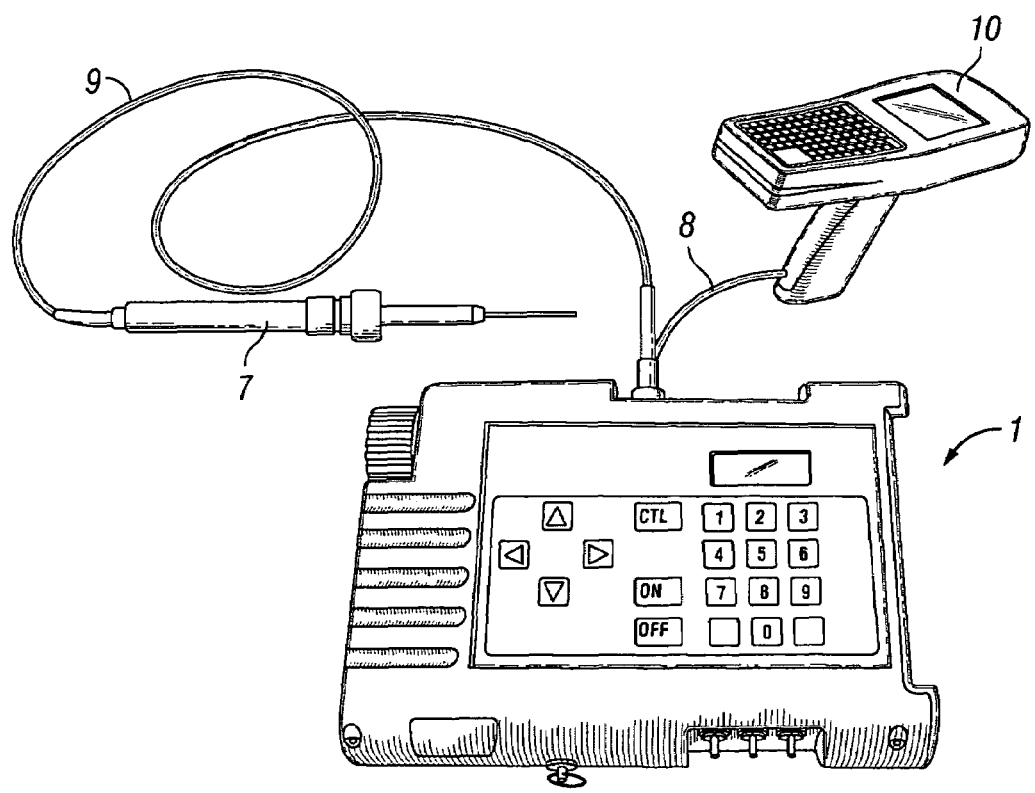
FIG. 2 illustrates prior art apparatus used to collect, transport and store vapor emission data.

FIG. 2 is block diagram that shows the current art used to capture Fugitive Emissions from petrochemical and refinery facilities. A gas collection probe 7 takes samples of air in the vicinity of piping sealed joints. Samples drawn into the collection probe are drawn into a tube or transport conduit 9 carrying the sample into the flame ionization detector chamber 2 illustrated in FIG. 1. Based on the content of fugitive gas present in the sample the flame ionization detector, a binary number is created with a value representative of the level of the fugitive gas present in the intake sample. This binary number is converted into a serial data stream by the flame ionization detector apparatus 1. The serial data stream is transmitted to a hand held data logging apparatus 10 over a wire data cable 8. Fugitive emission intensity is stored in a memory in the data logging apparatus. At the end of the test shift, fugitive emission data is transferred to a back office database as a permanent record.

Figure 3:
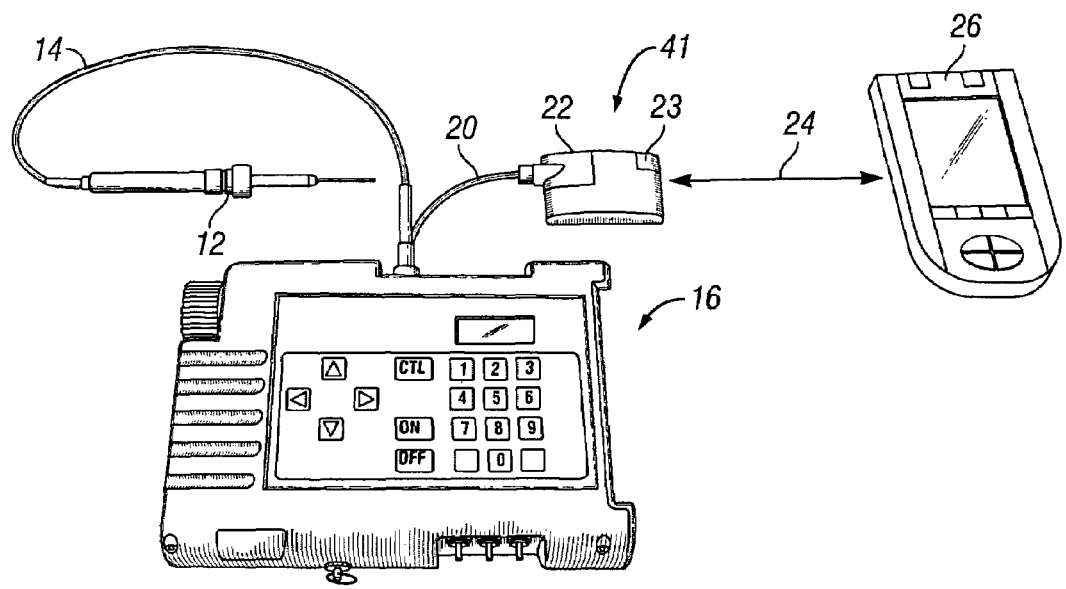
FIG. 3 illustrates in schematic format an embodiment of the present invention that collects, transports and stores emission data.

FIG. 3 is a block diagram that shows an embodiment of the present invention to improve the current art shown in FIG. 2. A gas collection probe 12 takes samples of air in the vicinity of piping sealed joints. Samples drawn into the collection probe are drawn into a tube or transport conduit 14 carrying the sample into the flame ionization detector chamber 2 (illustrated in FIG. 1) of a flame ionization detector or other emission measuring device 16. Based on the content of fugitive gas present in the sample, the emission measuring device creates a binary number with a value representative of the level of the fugitive gas present in the intake sample. This binary number is converted into a serial data stream by the emission measuring device using a microprocessor.

A serial data stream is sent over a short length of cable 20 of approximately twelve inches to a wireless data-logging adapter 41 with a, hard drive, or any digital storage medium 22. The storage medium 22 receives the fugitive emission in binary data format. The data is temporarily stored in a memory and a like copy of the fugitive emission sample is converted from a wired binary serial stream signal to a wireless binary stream signal by a transceiver 23 associated with the memory medium. The transceiver sends the fugitive emission sample data to a Personal Data Assistant 26, such as a data logger device, attached to the wrist of the test operator.

The short data cable 20 provides direct current power path to the storage medium and transceiver from the emission detector battery power supply.

In one embodiment of the present invention, the test operator initiates a taking of a fugitive emission sample by entering an instruction onto the Personal Data Assistant 26. The command to take a fugitive emission sample is sent back to the emission measuring device 16 by wireless transmission 24 to the transceiver 23 and then transfer information already stored to the PDA 26. Alternatively, the transceiver could relay an instruction back to the emission monitoring device 16 through the cable 20.

Figure 4:
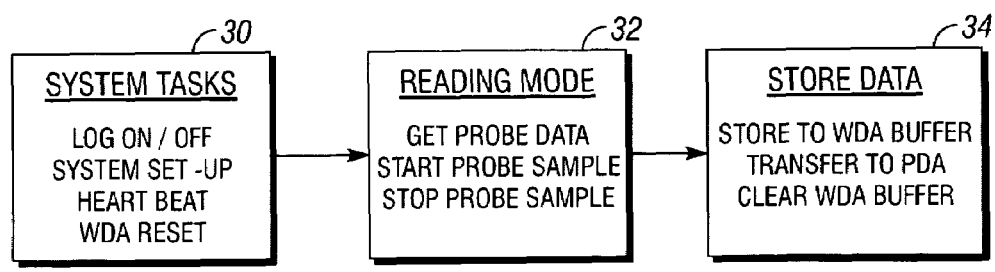
FIG. 4 illustrates in schematic operational state of an embodiment of the present invention.

FIG. 4 shows the operational states of an embodiment of the present invention. A state is present that performs administrative tasks. System task operations 30 represent shared administrative tasks between the Personal Data Assistant 26, the emissions monitoring device 16, and the WDA 41 apparatus. In the present invention manual commands initiated by the Test Operator are entered into the Personal Data Assistant 26. The storage medium is assigned as the Server and the Personal Data Assistant as the Client. It is the Server-/Client relationship that enables the Test operator manual commands and the transport of fugitive emission sample data to the Personal Data Assistant by way of the storage medium and associated transceiver.

In an embodiment of the present invention a system set-up state occurs when the Test operator turns power on the Personal Data Assistant. The emission measuring device and storage medium is power applied. This state initializes the Personal Data Assistant and the storage medium so that Test Operator initiator commands and fugitive emission sample data are enabled for operation.

The system tasks state requires a Test Operator to provide authentication by a Log On and Log Off procedure. Once authenticated the storage medium initiates a periodic 'Heart Beat' processes that provides validation that fugitive emission sample data is correctly being transferred from the to the storage medium and to the Personal Data Assistant. It also validates that manual commands initiated by the Test Operator are correctly sent to the storage medium with transceiver and to the emission measuring device.

A storage medium reset command is available to the Test Operator in any event when any of the apparatus shown in FIG. 3 becomes inoperative or unresponsive to Test Operator commands.

The System Tasks State 30 enables the Test Operator to begin a process of initiating the emission measuring device to take fugitive emission samples in the Reading Mode State 32. In Reading Mode 32, a Get Probe Data command is entered into the Personal Data Assistant 26 and interpreted by the software for the WDA 41 with transceiver to initialize the emission measuring device. The Test Operator enters Start Probe Sample to instruct the emission measuring device to sample and process for detecting fugitive emissions in the apparatus shown in figure 1. At the completion of the fugitive emissions sample period a Stop Probe Sample Command is entered into the Personal Data Assistant that is interpreted by the WDA 41 to disable the emission measuring device from taking further fugitive emission samples.

Figure 5:
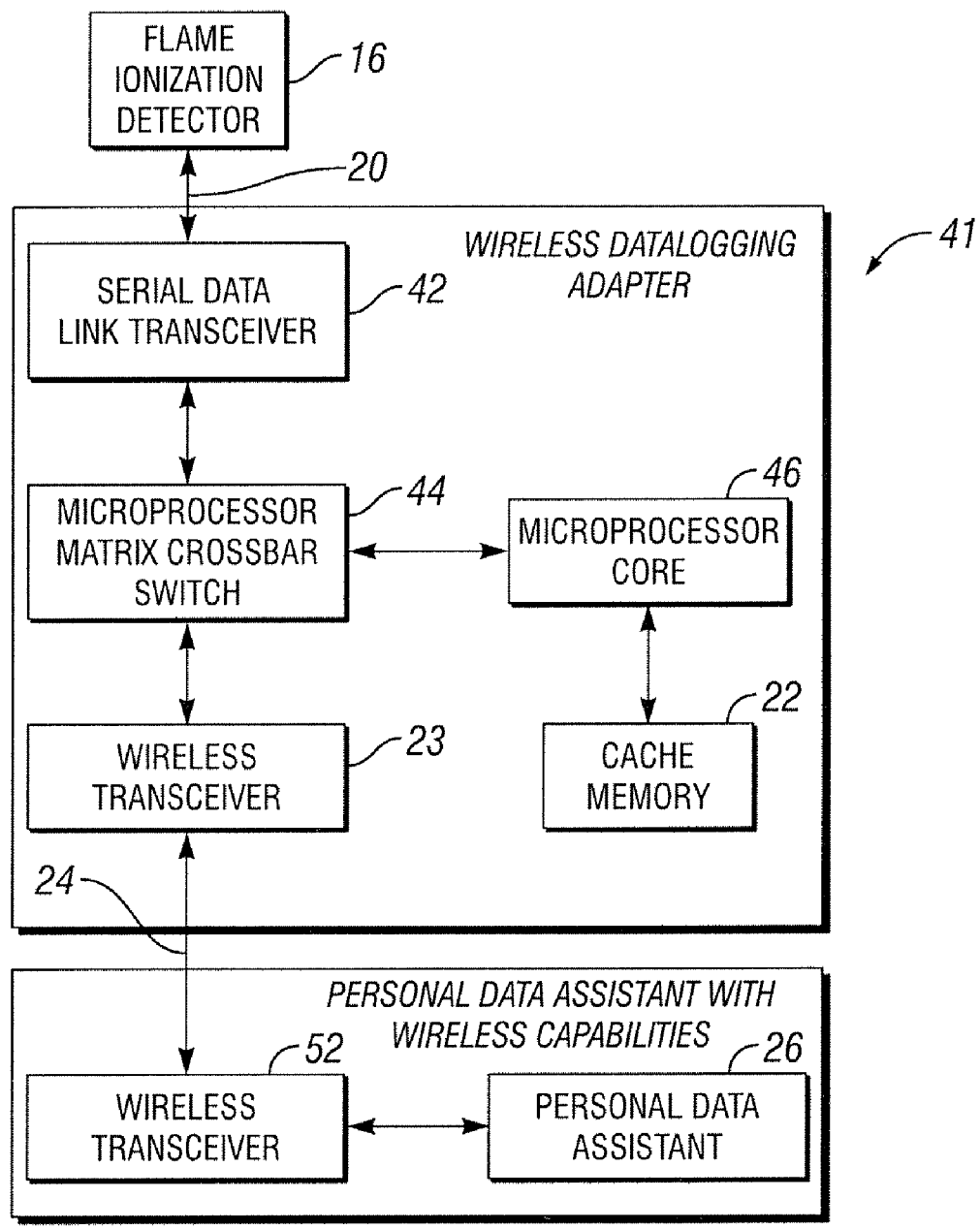
FIG. 5 shows an embodiment of the present invention with a wireless data logger.

As the emission measuring device takes in fugitive emissions samples and transfers emissions data to the WDA 41, the Store Data State 34 is enabled. The first action commands the emission measuring device to transfer fugitive emission sample data to a Cache Memory, shown in FIG. 5, located in the WDA 41. On command from the Test Operator fugitive emission sample data is transferred to the Personal Data Assistant over the Wireless Radio Link 24 shown in FIG. 3. In an alternative embodiment, the final command in the Store Data State instructs the Storage medium to clear the Cache Memory 22, shown in FIG. 5 to delete fugitive emission sample data.

Commands sent by the Personal Data Assistant to the wireless data logger adapter initiates taking fugitive emission samples and routing those samples to both the Cache Memory 22 in the Wireless data-logger and to the Wireless Server Transceiver, through the Wireless Data Link onto the Personal Data Assistant memory.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

An embodiment of the invention uses a probe to detect gas emissions. Such probe transports gasses encountered during a sampling period to an emissions measuring device via a transport conduit. The emissions measuring device is connected with a WDA 41 via a serial data link 20 (shown in FIG. 3). Such serial data link may be hardwired or wireless. The WDA 41 shown in FIG. 5 functions in conjunction with a cache memory 22 and a microprocessor 44 and 46 and a networking device 23. The networking device 23 functions as a transceiver capable of two way wireless communications, such as sending and receiving data streams. A data-logger 26 (e.g. a personal data assistant) exists as a separate unit. The data-logger device functions as a separate data retention device in that it has a storage medium, microprocessor and a networking device capable of two way wireless communications.

In another embodiment, during a sample period—the interval in which gas emissions are measured—a test operator causes the probe to survey sealed piping in search of fugitive gases. When such gases are encountered, gas enters the probe aperture and flows from the transport conduit into the measuring device 16 where flame ionization levels are evaluated and digitized. After digitizing the gas level into a serial data stream the storage medium 22 on the WDA 41 retains a copy of the data. A transceiver 23 on the WDA 41 then sends a redundant copy of the data wirelessly to the data logging device 26.

What is claimed is:
1. An apparatus for communicating and storing emissions data during the emissions measuring process comprising:
    a first portable light-weight human carriable device and a separate second portable light-weight human carriable device that cooperate as a single portable light-weight human carriable device;
    said first portable light-weight human carriable device comprising:
        (a) a sampling probe adapted to receive fugitive emissions;
        (b) a transport conduit having a first end, connected to the sampling probe, and a second end, wherein the transport conduit is configured to transport a sample of fugitive emissions from the sampling probe;
        (c) an emissions measuring device connected to the second end of the transport conduit, wherein the emissions measuring device is adapted to receive the sample of fugitive emissions and produce measurement data representing the sample of fugitive emissions; and
        (d) an adapter having a wireless transceiver operably connected to the emission measuring device, wherein the adapter is configured to transmit a signal representing the measurement data over a radio frequency by operation of the wireless transceiver; and said second portable light-weight human carriable device comprising a hand held personal data assistant having a wireless transceiver, wirelessly connected during the emissions measuring process to the adapter, wherein the personal data assistant is configured to receive the radio frequency signal representing the measurement data over the wireless connection.

2. The apparatus of claim 1 wherein the adapter and/or personal data assistant provides an indication when the wireless connection is dropped.

3. The apparatus of claim 1 wherein the adapter and/or personal data assistant provides an indication when the measurement data is stored.

4. The apparatus of claim 1 wherein the adapter and the personal data assistant each further comprise a storage medium, wherein each storage medium is configured to store the measurement data collected and monitored during the emissions measuring process.

5. The apparatus of claim 1 wherein the adapter and/or personal data assistant provides an indication when the signal representing the measurement data is transmitted over the wireless connection.

6. The apparatus of claim 1, wherein the emissions measuring device further comprises an ignition filament and the personal data assistant is configured to transmit a command to ignite the ignition filament.

7. The apparatus of claims 1 further comprising a microprocessor connected to the emissions measuring device, wherein the microprocessor is configured to determine a level of fugitive gas emissions collected by the sampling probe and convert the level to a signal for wireless transmission from the adapter to the personal data assistant.

8. The apparatus of claim 4 wherein the storage mediums of the adapter and the personal data assistant are configured to store redundant copies of the digital measurement data.

9. An apparatus for storing emissions data comprising:
a first portable light-weight human carriable device and a separate second portable light-weight human carriable device that cooperate as a single portable light-weight human carriable device;
said first light-weight portable human carriable device comprising:
(a) a sampling probe configured to collect a sample of fugitive emissions;
(b) a converter connected to the sampling probe, wherein the converter is configured to digitize the sample of fugitive emissions by producing digital measurement data representing the sample of fugitive emissions; and
(c) a first storage medium connected to the converter, wherein the first storage medium is configured to store the measurement data; and
said second light weight human carriable device comprising a second separate storage medium removably connected to the first storage medium over a wireless communications link; wherein the second storage medium stores a redundant copy of the measurement data.

10. The apparatus of claim 9 wherein the communications link is a radio frequency wireless connection.

11. The apparatus of claim 9 wherein the communications link is connected to the first storage medium or the converter.

12. An apparatus for transmitting emissions data over a wireless communications link comprising:
a first portable light-weight human carriable device and a separate second portable light-weight human carriable device that cooperate as a single portable light-weight human carriable device;
said first light weight portable human carriable device comprising;
(a) a sampling probe configured to collect a sample of fugitive emissions;
(b) a converter connected to the sampling probe, wherein the converter is configured to digitize the sample of fugitive emissions by producing digital measurement data representing the sample of fugitive emissions; and
(c) a transceiver connected to the converter, wherein the transceiver is configured to wirelessly transmit a radio frequency signal representing the measurement data over a wireless communications link during the emissions measuring process; and
said second light-weight portable human carriable device comprising a portable personal data assistant, removably connected to the transceiver over the wireless communication link, wherein the personal data assistant is configured to receive the radio frequency signal representing the measurement data.

13. The apparatus of claim 12 further comprising a first storage medium connected to converter, wherein the first storage medium is configured to store the measurement data.

14. The apparatus of claim 13 further comprising a second storage medium connected to the personal data assistant, wherein the second storage medium is configured for redundant storage of the measurement data.

15. The apparatus of claim 14 wherein the second storage medium is removably connected to the first storage medium over the wireless communications link.

* * * * *